United States Patent [19]

Polsky et al.

[11] 4,280,488
[45] Jul. 28, 1981

[54] ANKLE SUPPORT WITH ELASTIC PANEL

[75] Inventors: Robert D. Polsky, Berkeley; Alexis G. Daneman, Danville, both of Calif.

[73] Assignee: Orthopedic Technology, Inc., San Leandro, Calif.

[21] Appl. No.: 90,801

[22] Filed: Nov. 2, 1979

[51] Int. Cl.³ ............................................. A61F 3/00
[52] U.S. Cl. .................................. 128/80 H; 128/166
[58] Field of Search .............................. 128/80 H, 166

[56] References Cited

U.S. PATENT DOCUMENTS

| | | | |
|---|---|---|---|
| 999,010 | 7/1911 | Collis | 128/166 |
| 1,027,897 | 5/1912 | Quenzer | 128/166 |
| 1,090,906 | 3/1914 | Collis | 128/166 |
| 2,994,322 | 8/1961 | Cullen et al. | 128/80 H |
| 3,073,305 | 1/1963 | Biggs, Jr. et al. | 128/80 H X |
| 3,970,083 | 7/1976 | Carrigan | 128/166 |
| 4,187,844 | 2/1980 | Caprio, Jr. | 128/166 |

*Primary Examiner*—John D. Yasko
*Attorney, Agent, or Firm*—Townsend and Townsend

[57] ABSTRACT

The disclosed invention is an improved semi-rigid, ankle support generally conforming to the instep, ankle, and lower leg, and wearable inside a shoe, said support being comprised of one or more non-elastic panels and one or more elastic panels extending at least part of the length of said support, whereby the ankle is largely supported and immobilized, yet the support conforms to the foot, ankle, and lower leg and does not significantly reduce ankle function.

Preferably, the support is comprised of a largely sock-shaped unit closable at the front, defining apertures through which the heel and the toes extend, and sometimes including stays to improve the support given the ankle. This unit is formed of panels of non-elastic material and at least one panel of elastic material, preferably three such elastic panels. One elastic panel is usually located on each side of the unit and extends substantially the length of the entire unit, and one elastic panel is located in the center back of the unit and extends the length thereof. The side elastic panels are preferably comprised of sequentially overlapping sections of elastic material, each section aligned so that the direction of elastic stretch is generally normal to the axis of the leg or foot adjacent the section, and the back elastic panel is preferably comprised of one double-thick section of elastic material similarly aligned.

7 Claims, 5 Drawing Figures

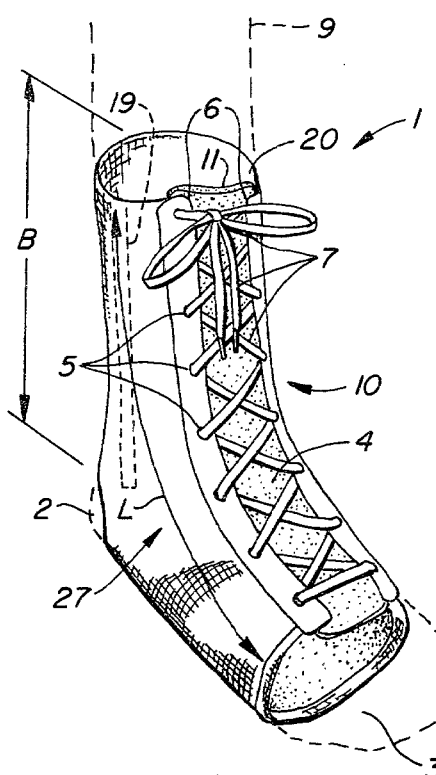
FIG._1A.
PRIOR ART
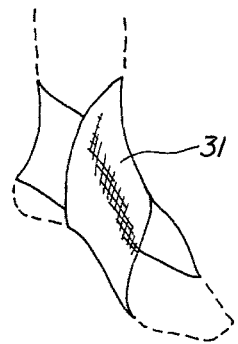
FIG._1B.
PRIOR ART
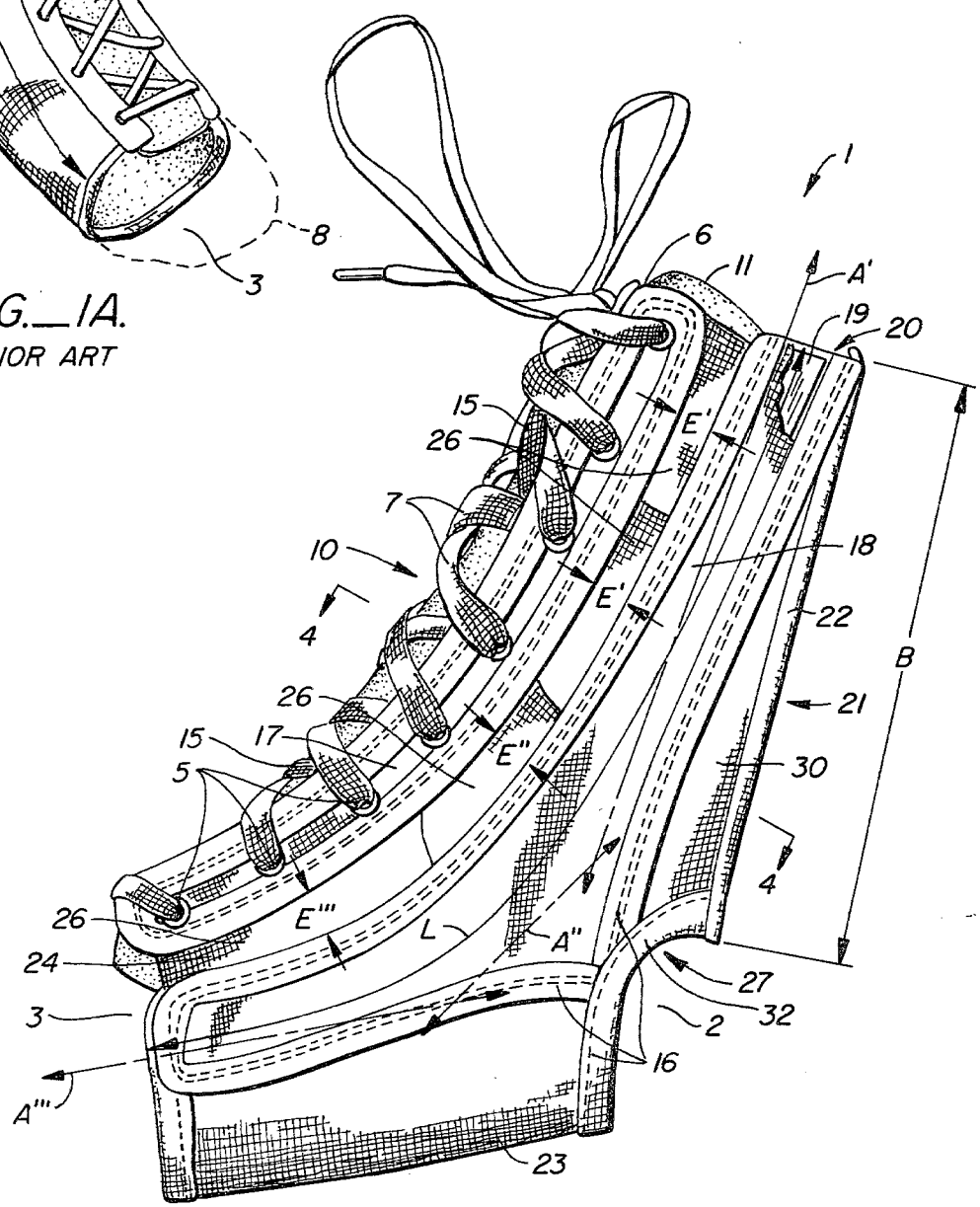
FIG._2.

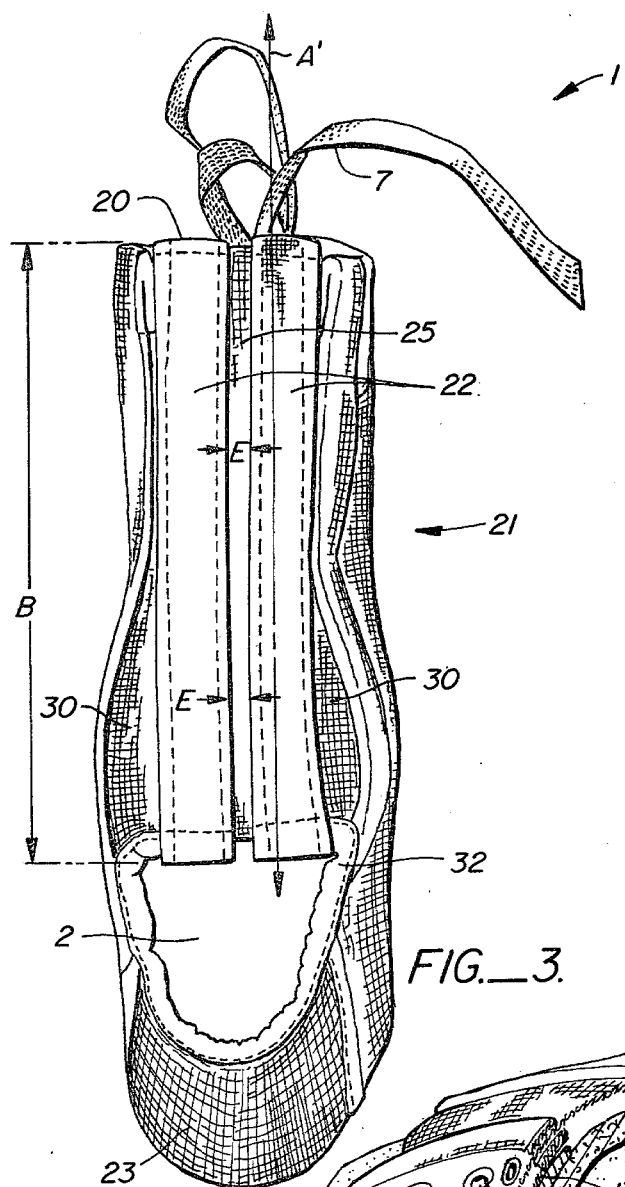
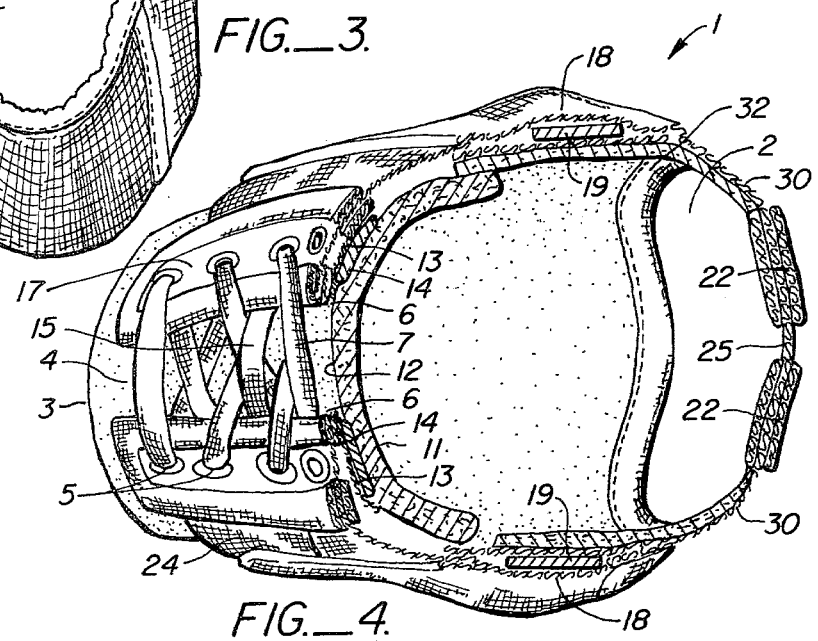

ANKLE SUPPORT WITH ELASTIC PANEL

BACKGROUND OF THE INVENTION

1. Field of the Invention

This invention relates to ankle splints and supports used to support a weak ankle, generally immobilize the ankle in case of a minor fracture, a sprain, or the like, or prevent such fractures, sprains and the like.

2. Summary of the Prior Art

In the past, two general types of ankle supports have been used for the above purposes. The first type is generally formed entirely of elastic pulled taut around and closely conforming to the ankle, usually the foot, ankle, and lower leg. Such supports may or may not enclose the toe and heel. Generally, these supports have been formed of knitted or woven elastic, elastic wrap, or elastic tape.

Although such supports are relatively comfortable, can easily be worn inside a shoe, and do not significantly reduce ankle function, they generally do not immobilize the ankle sufficiently to truly protect it. In addition, if not properly wrapped, some may either cut off circulation if they are too tight or provide virtually no support if they are too loose. Furthermore, they frequently deteriorate after one or a few uses so that less ankle support is provided.

The second type of ankle supports known in the art are non-elastic, generally semi-rigid supports or splints which can be composed of a variety of materials such as foam, laminates, vinyl, canvas, or leather. Such splints are usually comprised of a largely sock-shaped unit, usually openable down the front and which surrounds the instep, ankle, and lower leg, but does not enclose the toes and heel.

These units frequently include one or more sometimes removable stays located in and extending down the side of the splint. An additional stay is usually also included extending substantially the length of the front of the splint. These such stays reinforce and improve the rigidity of the splint. Where the unit is closable at the front by means of laces, the latter stay is usually included on a tongue interior to the laced area, which tongue improves the fit of the splint and reduces chafing.

Although these semi-rigid splints are quite effective in immobilizing and protecting the ankle, they are generally not wearable inside a shoe, and they significantly reduce ankle function so as to generally prevent heavy work, athletic activities, or the like while they are worn.

SUMMARY OF THE INVENTION

The present invention is a semi-rigid ankle support generally conforming to the instep, ankle, and lower leg and wearable inside a shoe which minimizes the above disadvantages of prior semi-rigid and non-rigid ankle supports. The present splint includes one or more elastic panels together with one or more non-elastic panels extending at least part of the length of the splint. The elastic panels reduce the slack otherwise inherent in prior semi-rigid splints, to provide good conformation of the splint to the limb. The support of the present invention thus provides both the immobilizing effect of prior semi-rigid splints and the conformability of prior non-rigid supports; it is wearable inside a normal shoe, functioning to both protect and support the ankle but allowing flexibility of ankle movement so as to permit vigorous activity on a weakened ankle without significant loss of ankle function.

In the preferred embodiment, the present splint includes a largely sock-shaped unit having an openable front and removable semi-rigid stays down the sides and front of the unit. The preferred unit includes non-elastic panels together with three elastic panels, two elastic panels extending substantially the length of the entire splint, one located on each side of the splint and extending parallel to the openable area, and a third elastic panel extending the length of the splint at the center back. Each side elastic panel is preferably comprised of separate sequentially overlapping sections of elastic material, each section extending a portion of the length of the entire panel and being aligned so that the direction of elastic stretch is generally normal to the axis of the leg and/or foot adjacent the section. The center back elastic panel is preferably comprised of one piece of elastic material of double thickness with the direction of stretch generally normal to the axis of the lower leg. The set of so aligned sections of elastic material particularly promotes close conformation of the splint to the instep, ankle, and leg to provide excellent ankle support akin to that provided by an elastic bandage, while the splint as a whole generally immobilizes the ankle.

BRIEF DESCRIPTION OF THE DRAWINGS

FIG. 1A is a perspective view of a prior art semi-rigid ankle splint.

FIG. 1B is a perspective view of a prior art elastic ankle support.

FIG. 2 is a side view of the improved ankle splint of the present invention particularly illustrating one of the elastic panels on the side of the splint.

FIG. 3 is a back view of the improved ankle splint of the present invention particularly illustrating the back elastic panel.

FIG. 4 is a cross section of the ankle splint of the present invention taken at lines 4—4 of FIG. 2 and particularly illustrating the construction of the ankle splint of the present invention.

DESCRIPTION OF THE SPECIFIC EMBODIMENTS

A prior semi-rigid ankle splint wearable inside a shoe is illustrated in FIG. 1A. Such prior splints commonly included a semi-rigid, largely sock-shaped unit 1 defining apertures 2 and 3 therein through which the heel (at 2) and the toe (at 3) extend. The unit 1 was openable down the front 10, for example by defining a gap 4 extending the length of the front 10 and a series of apertures 5 extending along the length of the unit adjacent the gap edges 6 to hold laces 7 by which the splint is laced taut around the instep, ankle, and lower leg. Such splints also frequently included metal or plastic stays 19 to reinforce the splint and provide added ankle support. One or more stays were usually located on each side 27 of the unit, usually extending from the upper edge 20 of the splint down the side 27 and over the ankle bone. A tongue 11 also frequently reinforced by a stay, was also usually included interior to the gap 4 and extending the length of the splint front 10 to improve the splint's fit and reduce chafing.

Referring to FIG. 1B, one elastic ankle support of the prior art can be seen. The elastic support shown consists of an elastic wrap 31 wrapped around and conforming closely to the ankle, instep and lower leg.

The present invention, an improved semi-rigid ankle splint or support wearable inside a shoe and having at least one non-elastic panel and at least one elastic panel extending at least partially the length of the splint can be seen in FIGS. 2, 3, and 4.

The preferred splint includes a largely sock-shaped unit 1 generally conforming to the instep, ankle and lower leg and preferably defining apertures 2 and 3 through which the heel (at 2) and the toes (at 3) extend. The unit 1 is preferably openable down the front 10 and includes closure means to close the opening. A number of closure means, such as a velcro closure or a laced closure can be used. The figures illustrated a laced closure, the unit defining a gap 4 extending the entire length of the front 10 of the splint and also defining a series of (usually reinforced) apertures 5 extending the length L of the splint adjacent the gap edges 6, and the splint including laces 7 by which the unit is held generally taut around and generally conforming to the instep, ankle, and lower leg. To prevent chafing and to improve the fit of the splint, a tongue 11, preferably of felt, may extend the length of the front 10 of the splint interior to the gap 4. Preferably, two strips of canvas 15 are anchored at each end to the tongue 11 so that laces 7 can be laced between strips 15 and tongue 11 to secure tongue 11 in place in relation to the remainder of the splint.

The unit usually also includes conventional reinforcing stays frequently of plastic or metal, and preferably removable so the splint can be worn with or without them. Usually one or more stays 19 are located in and extending down each side 27 of the unit and one stay 14 is located in and extends substantially the length of the front of the unit. In the preferred embodiment, the front stay 14 is anchored to and extends substantially the length of the tongue exterior to the center front of the leg and foot by means of stitched down stay pockets 13, preferably of canvas. Usually the tongue is also provided with an additional stay pocket 13 interior to the center front so that the same splint can be used for each foot with the stay 14 itself being insertable in either pocket. In the preferred embodiment, canvas strips 15 are anchored between the stay pockets and the tongue.

Unit 1 is preferably formed of separate elastic and non-elastic panels extending the length of the splint and anchored together by heavy stitching 16. The non-elastic panels can be composed of the numerous materials appropriate for prior semi-rigid splints, and in the preferred embodiment are composed of a strong fabric-like material such as cotton-lined canvas or vinyl. Preferably, two such non-elastic panels 17 are located adjacent the gap 4 and two non-elastic panels 18 are separated from panels 17 by elastic panels 24. Each panel 18 includes an envelope enclosing stay 19, which stay extends from the upper edge 20 of the unit down the side 27 and over the ankle bone. Preferably, non-elastic panels 30 extend from panels 18 to the back 21 of the splint where they are attached to non-elastic panels 22, preferably separated from each other by elastic panel 25. Another non-elastic panel 23 extends from one panel 18 under the foot to the other panel 18. Ribbing 32 is usually included around the heel aperture 2 to reinforce the unit and prevent tearing or the like.

In the preferred embodiment of the present invention, unit 1 includes the three elastic panels already mentioned, two elastic panels 24 extending the entire length L of the splint between non-elastic panels 17 and 18, and one elastic panel 25 extending the entire length B of the center back portion 21 of the splint between non-elastic panels 22. These elastic panels improve the conformity of the splint to the instep, ankle, and lower leg to allow the splint to provide excellent ankle support without a significant reduction in ankle function.

The center back elastic panel 25 is preferably comprised of one section of elastic material, preferably double-thick, aligned so that the direction of elastic stretch E is substantially normal to the axis A' of the lower leg. Because it provides elastic, rather than rigid material extending over the Achilles tendon, it allows comfortable movement without restriction of that tendon. The preferred elastic material for this back elastic panel is double-thick heavyweight woven or knit elastic having between about 24 and 40 pick counts/sq.in.

Preferably, the side elastic panels 24 are comprised of several sequentially overlapping sections 26 of elastic material, each separate section 26 of elastic material being aligned so that the direction of elastic stretch (E'), (E'') and E''') is substantially normal to the axis A', A'', or A''' of the instep, ankle, or lower leg respectively, located adjacent that section of elastic material. In the preferred embodiment, there are four such sections 26 of elastic material, each extending approximately one-quarter of the length of the entire panel. The uppermost section 26 is preferably composed of medium weight elastic, and is primarily decorative. The three lower sections are preferably composed of medium weight woven or knit elastic of about 9 to 20 pick counts/sq.in.

The particular alignment of the elastic panels with the direction of elastic stretch substantially normal to the axis of the instep, ankle and leg causes the splint to conform even more closely to the limb, thereby further improving the support provided to the ankle, and further simulating the supportive but non-restricting effect of an elastic ankle bandage.

It will be understood that the above description and the drawings are intended by way of illustration and not by way of limitation, that various modifications in the invention will be apparent to those skilled in the art.

What is claimed is:

1. In a semi-rigid ankle support having a largely sock-like shape, said support having a back, a front, and two side portions, the improvement which comprises two elastic panels extending substantially the length of said support, one of said panels being included in each side portion of said support, each panel including substantially overlapping sections of elastic material, each section being aligned so that the direction of elastic stretch of said section is substantially normal to the axis of the leg or foot located adjacent said section of elastic material.

2. The improvement in an ankle support according to claim 1 from wherein said ankle support includes a generally sock-shaped unit openable at the front and further includes closure means adapted to hold said unit closed at the front, generally taut and generally conforming to the instep, ankle, and lower leg.

3. In a semi-rigid ankle support having a largely sock-like shape, said support having a back, a front, and two side portions, wherein said sock-shaped unit is openable at the front and includes closure means adapted to hold said unit closed at the front, generally taut and generally conforming to the instep ankle and lower leg, the improvement which comprises first, second and third elastic panels, said first panel forming part of and extending the length of said back portion of said support, said first elastic panel being aligned so that the direction of elastic stretch is substantially normal to the axis of the lower leg, each of said second and third panels forming a part of a respective side portion of said unit of said support and extending the length of said support.

4. A semi-rigid ankle splint wearable within a shoe comprising:
- a largely sock-shaped unit generally conforming to the instep, ankle, and lower leg, having a back, a front, and two side portions, and defining apertures through which the heels and toes extend, said unit also defining a gap extending the length of the front portion thereof and a series of apertures extending the length of the front portion thereof generally adjacent the edges of said gap and designed to receive laces;
- laces threaded through said series of apertures;
- a tongue secured interior to said gap;
- three stays, one of said stays detachably affixed to said unit at each side portion thereof and extending partially the length of said side portion, and a third of said stays detachably affixed to said tongue and extending substantially the length thereof;
- wherein said unit is comprised of a plurality of panels of a non-elastic material and three panels of elastic material, said panels being mutually attached to form said unit, one of said elastic panels located in each side portion of said unit and extending the length of said unit parallel to said gap, each of said side elastic panels comprised of sequentially overlapping sections of elastic material aligned with the direction of elastic stretch of each said section substantially normal to the axis of the leg or foot adjacent said section, and one elastic panel located in the center back portion of said unit, extending the length thereof, and formed of one section of elastic material aligned with the direction of elastic stretch substantially normal to the axis of the leg whereby said splint substantially supports the ankle without significantly reducing ankle function.

5. A semi-rigid ankle support wearable within a shoe comprising:
- a largely sock-shaped unit generally conforming to the instep, ankle, and lower leg and having a back, a front, and two side portions, defining apertures through which the heel and toes extend, said unit being openable at the front;
- closure means adapted to hold said unit closed at the front and generally taut around the instep, the ankle, and lower leg;
- wherein said unit is comprised of panels of non-elastic material and three panels of elastic material, said panels of non-elastic and elastic materials being attached together to form said unit, one of said elastic panels being located in each side portion of said unit and extending the length of said unit, and one of said elastic panels located in the center back portion of said unit and extending the length thereof
- whereby said splint substantially supports the ankle without significantly reducing ankle function.

6. An ankle splint according to claim 5 and wherein said elastic panels located in the side portion of said unit are comprised of sequentially overlapping sections of elastic material, each section aligned with the direction of elastic stretch substantially normal to the axis of the leg or foot adjacent said section whereby conformation of the splint to the foot and leg is improved and support to the ankle is increased.

7. An ankle splint according to claim 6 and wherein each of said side elastic panels includes at least three of said overlapping sections.

* * * * *